US012746029B2

(12) United States Patent
Akagane

(10) Patent No.: US 12,746,029 B2
(45) Date of Patent: Sep. 29, 2026

(54) ULTRASOUND TREATMENT TOOL

(71) Applicant: OLYMPUS MEDICAL SYSTEMS CORP., Tokyo (JP)

(72) Inventor: Tsunetaka Akagane, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 311 days.

(21) Appl. No.: 18/439,086

(22) Filed: Feb. 12, 2024

(65) Prior Publication Data

US 2024/0268854 A1 Aug. 15, 2024

Related U.S. Application Data

(60) Provisional application No. 63/484,611, filed on Feb. 13, 2023.

(51) Int. Cl.
*A61B 17/32* (2006.01)
*A61B 17/00* (2006.01)

(52) U.S. Cl.
CPC ................. *A61B 17/320092* (2013.01); *A61B 2017/0084* (2013.01); *A61B 2017/00853* (2013.01); *A61B 2017/320082* (2017.08); *A61B 2017/320094* (2017.08)

(58) Field of Classification Search
CPC ............ A61B 17/32; A61B 17/320068; A61B 17/320092; A61B 2017/00831; A61B 2017/0084; A61B 2017/00849; A61B 2017/00853; A61B 2017/2825; A61B 2017/320082; A61B 2017/320094; A61B 2017/320095; A61B 18/1445; A61B 2018/00589; A61B 2018/00595; A61B 2018/00601; A61B 2018/00607; A61B 2018/0063; A61B 2018/00994
See application file for complete search history.

(56) References Cited

U.S. PATENT DOCUMENTS

2016/0010802 A1 1/2016 Leavitt et al.
2016/0213395 A1 7/2016 Anim
2016/0374744 A1* 12/2016 Akagane ................ A61B 18/14 606/27
2017/0119425 A1* 5/2017 Hibner ........... A61B 17/320092
(Continued)

FOREIGN PATENT DOCUMENTS

JP 2007527747 A 10/2007
JP 2009509775 A 3/2009
(Continued)

*Primary Examiner* — Robert A Lynch
(74) *Attorney, Agent, or Firm* — Schwegman Lundberg & Woessner, P.A.

(57) ABSTRACT

An ultrasound treatment tool includes: an ultrasound blade including a treatment portion located at a distal end of the ultrasound blade, a jaw configured to open and close relative to the treatment portion. The jaw includes: a surface, a contact surface facing the ultrasound blade, the contact surface configured to be in contact with the treatment portion when the jaw is closed relative to the treatment portion. The contact surface comprises: a first resin layer positioned on the surface, the first resin layer formed of a first resin, a second resin layer layered over the first resin layer, the second resin layer formed of a mixed resin, the mixed resin being a mixture of a second resin and the first resin.

17 Claims, 6 Drawing Sheets

(56) References Cited

U.S. PATENT DOCUMENTS

| | | | |
|---|---|---|---|
| 2017/0164972 | A1 | 6/2017 | Johnson et al. |
| 2019/0133636 | A1 | 5/2019 | Morisaki |
| 2020/0009299 | A1 | 1/2020 | Anim |
| 2022/0039858 | A1 | 2/2022 | Johnson et al. |

FOREIGN PATENT DOCUMENTS

| | | | |
|---|---|---|---|
| JP | 2018503462 | A | 2/2018 |
| JP | 2019500101 | A | 1/2019 |
| WO | WO-2007044327 | A2 | 4/2007 |
| WO | WO-2018011918 | A1 | 1/2018 |

* cited by examiner

ULTRASOUND TREATMENT TOOL

CROSS-REFERENCE TO RELATED APPLICATION

This application is based on and claims priority under 35 U.S.C. § 119 to U.S. Provisional Application No. 63/484,611, filed Feb. 13, 2023, the entire contents of which are incorporated herein by reference.

BACKGROUND

1. Technical Field

The present disclosure relates to ultrasound treatment tools.

2. Background

An ultrasound treatment tool, which may be used for treatment of a region to be treated (hereinafter, referred to as a treatment target) in a body tissue by application of ultrasound energy to the treatment target, has been known conventionally (see, for example, International Publication WO No. 2018/011918).

An ultrasound treatment tool described in International Publication WO No. 2018/011918 includes a rod portion, a holder portion, and a pad portion (hereinafter, referred to as a contact portion), which are described below.

The rod portion has, at a distal end thereof, a treatment portion for treatment of a treatment target, and transmits ultrasound vibration from a proximal end thereof toward the treatment portion. The holder portion is opened and closed, relatively to the treatment portion.

The contact portion is a structural body formed of a resin and is attached to the holder portion. The contact portion grasps the treatment target between the contact portion and the treatment portion.

SUMMARY

In some examples, an ultrasound treatment tool may include an ultrasound blade that includes a treatment portion at a distal end of the ultrasound blade, the treatment portion being configured to treat a body tissue. The ultrasound blade can be configured to transmit ultrasound vibration from a proximal end of the ultrasound blade toward the treatment portion. The ultrasound treatment tool may further include grasping portion that may be opened and closed relatively to the treatment portion. The grasping portion can be configured to grasp the body tissue between the grasping portion and the treatment portion. The ultrasound treatment tool may further include a contact portion provided at the grasping portion. The contact portion can be configured to be in contact with the treatment portion when the grasping portion is closed relatively to the treatment portion. The contact portion may include a first resin portion formed of a first resin and a second resin portion layered over the first resin portion. The second resin portion may be positioned on a treatment portion side with respect to the first resin portion, and formed of a mixed resin that is obtained by mixing a second resin into the first resin.

In some examples, an ultrasound treatment tool includes an ultrasound blade may include a treatment portion located at a distal end of the ultrasound blade, a jaw configured to open and close relative to the treatment portion. The jaw may include a surface, a contact surface facing the ultrasound blade, the contact surface configured to be in contact with the treatment portion when the jaw is closed relative to the treatment portion. The contact surface may comprise a first resin layer positioned on the surface, the first resin layer formed of a first resin, a second resin layer layered over the first resin layer, the second resin layer formed of a mixed resin, the mixed resin being a mixture of a second resin and the first resin.

In some examples, an ultrasound treatment tool may include an ultrasound blade including a treatment portion located at a distal end of the ultrasound blade and a jaw configured to open and close relative to the treatment portion. The jaw may include a surface and a contact surface facing the ultrasound blade. The contact surface may be configured to be in contact with the treatment portion when the jaw is closed relatively to the treatment portion. The contact surface may comprise a first resin layer positioned on the surface, the first resin layer formed of a first resin, the first resin layer having a first thickness and a second resin layer layered over the first resin layer, the second resin layer formed of a second resin, the second resin layer having a second thickness, and wherein the second thickness is smaller than a first thickness.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Modes for implementing the disclosure (hereinafter, embodiments or examples) will be described herein while reference is made to the drawings. The disclosure is not limited by the examples described herein. Like portions will be assigned with like reference signs, throughout the drawings.

Schematic Configuration of Treatment System

Figure 1:
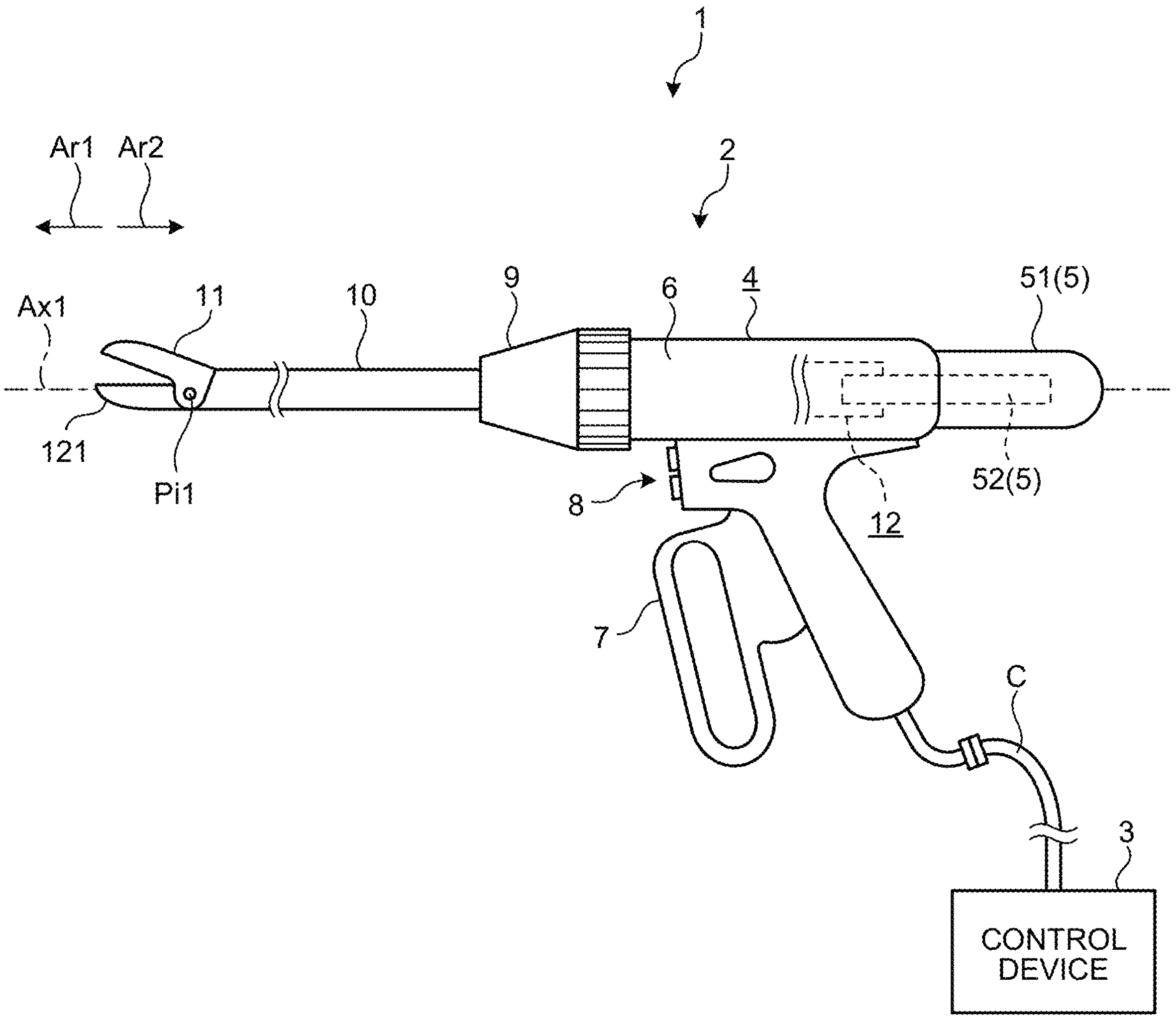
FIG. 1 is a diagram illustrating a treatment system according to an embodiment.

FIG. 1 is a diagram illustrating a treatment system 1 according to an embodiment.

The treatment system 1 may be for treatment of a part to be treated (hereinafter, referred to as a treatment target) in a body tissue by application of treatment energy to the treatment target. The treatment energy according to the embodiment may include ultrasound energy and high frequency energy. Furthermore, the treatment that is able to be executed by the treatment system 1 according to the embodiment may be, for example, coagulation (sealing) of the treatment target or incision of the treatment target. Furthermore, the coagulation and the incision may be performed at the same time. The treatment energy to be applied to the treatment target is not necessarily both ultrasound energy and high frequency energy and may be just ultrasound energy or may just be high frequency energy. This treatment system 1 includes, as illustrated in FIG. 1, an ultrasound treatment tool 2 and a control device 3.

Configuration of Ultrasound Treatment Tool

Hereinafter, one of directions along a central axis Ax1 (FIG. 1) of a sheath 10 will be referred to as a distal direction, "Ar1", and the other direction will be referred to as a proximal direction, "Ar2". Furthermore, a "width direction" referred to hereinafter means a direction orthogonal to the central axis Ax1 and to directions a jaw 11 is opened and closed relatively to a treatment portion 121, the direction being orthogonal to the plane of paper of FIG. 1 and FIG. 2 and lateral in FIG. 3.

Figure 2:
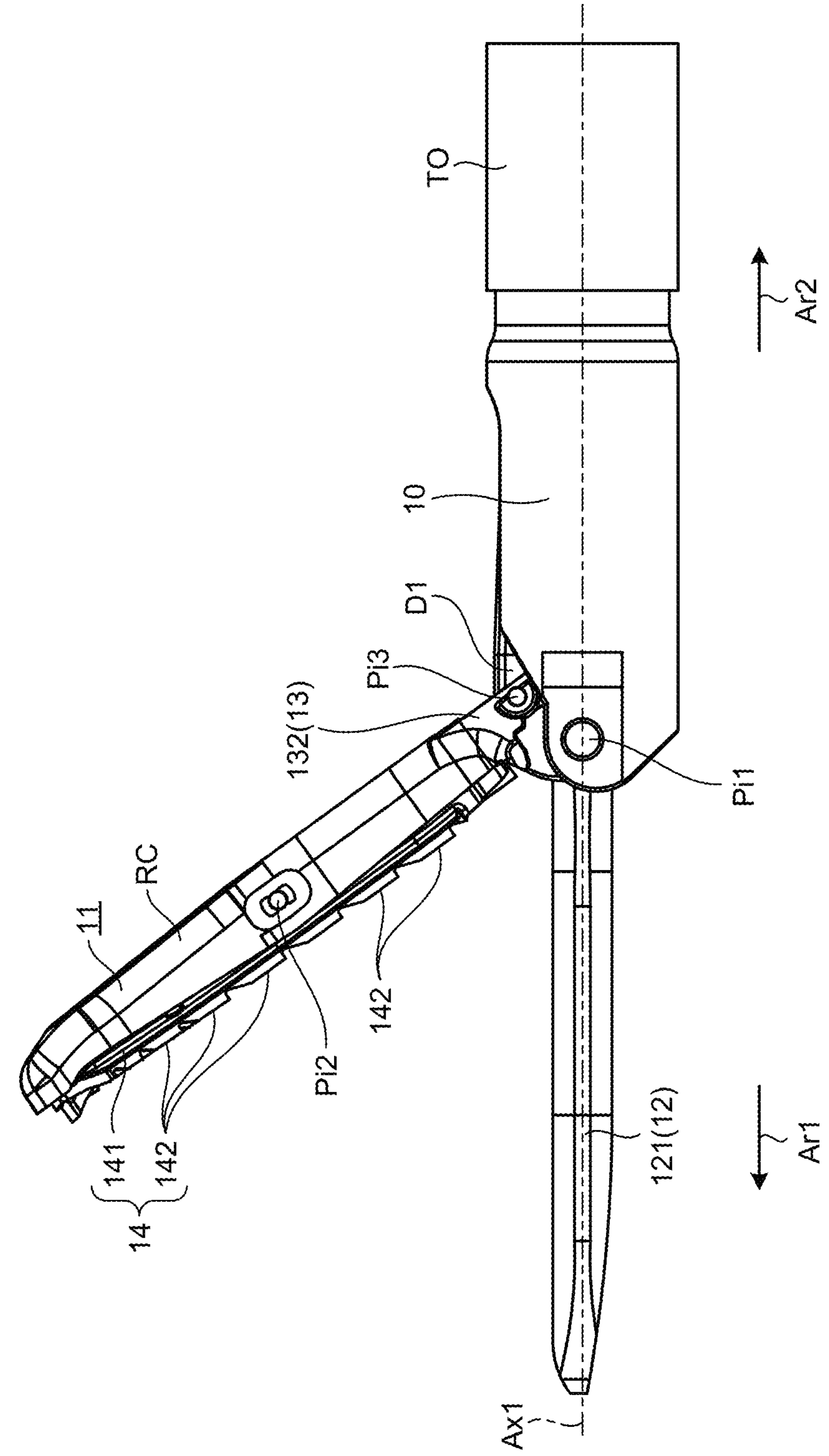
FIG. 2 is a diagram illustrating a distal end portion of an ultrasound treatment tool.

FIG. 2 is a diagram illustrating a configuration of a distal end portion of the ultrasound treatment tool 2. Specifically, FIG. 2 is a diagram of the distal portion of the ultrasound treatment tool 2 as viewed along the width direction.

The ultrasound treatment tool 2 may be a treatment tool for treatment of a treatment target by application of ultrasound energy and high frequency energy to the treatment target. This ultrasound treatment tool 2 may include, as illustrated in FIG. 1, a handpiece 4 and an ultrasound transducer unit 5.

The handpiece 4 may include, as illustrated in FIG. 1 and FIG. 2, a holding case 6 (FIG. 1), an operation handle 7 (FIG. 1), one or more switches 8 (FIG. 1), a rotation knob 9 (FIG. 1), the sheath 10, the jaw 11, and an ultrasound blade 12.

The holding case 6 may support the whole or the entire ultrasound treatment tool 2.

The operation handle 7 may be movably attached to the holding case 6 and receive opening and closing operation from an operator, such as an operating surgeon.

The one or more switches 8 are provided in a state of being exposed to the exterior of the holding case 6 and receive treatment operation from an operator, such as an operating surgeon.

The rotation knob 9 may have an approximately cylindrical shape coaxial with the central axis Ax1 and may be provided near an end of the holding case 6, the end being in the distal direction Ar1. The rotation knob 9 can receive rotating operation from an operator, such as an operating surgeon. The rotating operation can cause the rotation knob 9 to rotate about the central axis Ax1, relative to the holding case 6. Furthermore, rotation of the rotation knob 9 can cause the sheath 10, the jaw 11, and the ultrasound blade 12 to rotate about the central axis Ax1.

The sheath 10 may be a cylindrical pipe formed of an electrically conducting material, such as a metal.

A first pin "Pi1" (FIG. 1 and FIG. 2) that extends in the width direction and is cylindrical can be fixed to an end portion of the sheath 10, the end portion being in the distal direction Ar1.

An outer peripheral surface of the sheath 10 may be covered with an electrically insulating outer tube "TO" (FIG. 2). Furthermore, an inner peripheral surface of the sheath 10 may be covered with an electrically insulating inner tube (not illustrated in the drawings).

Figure 3:
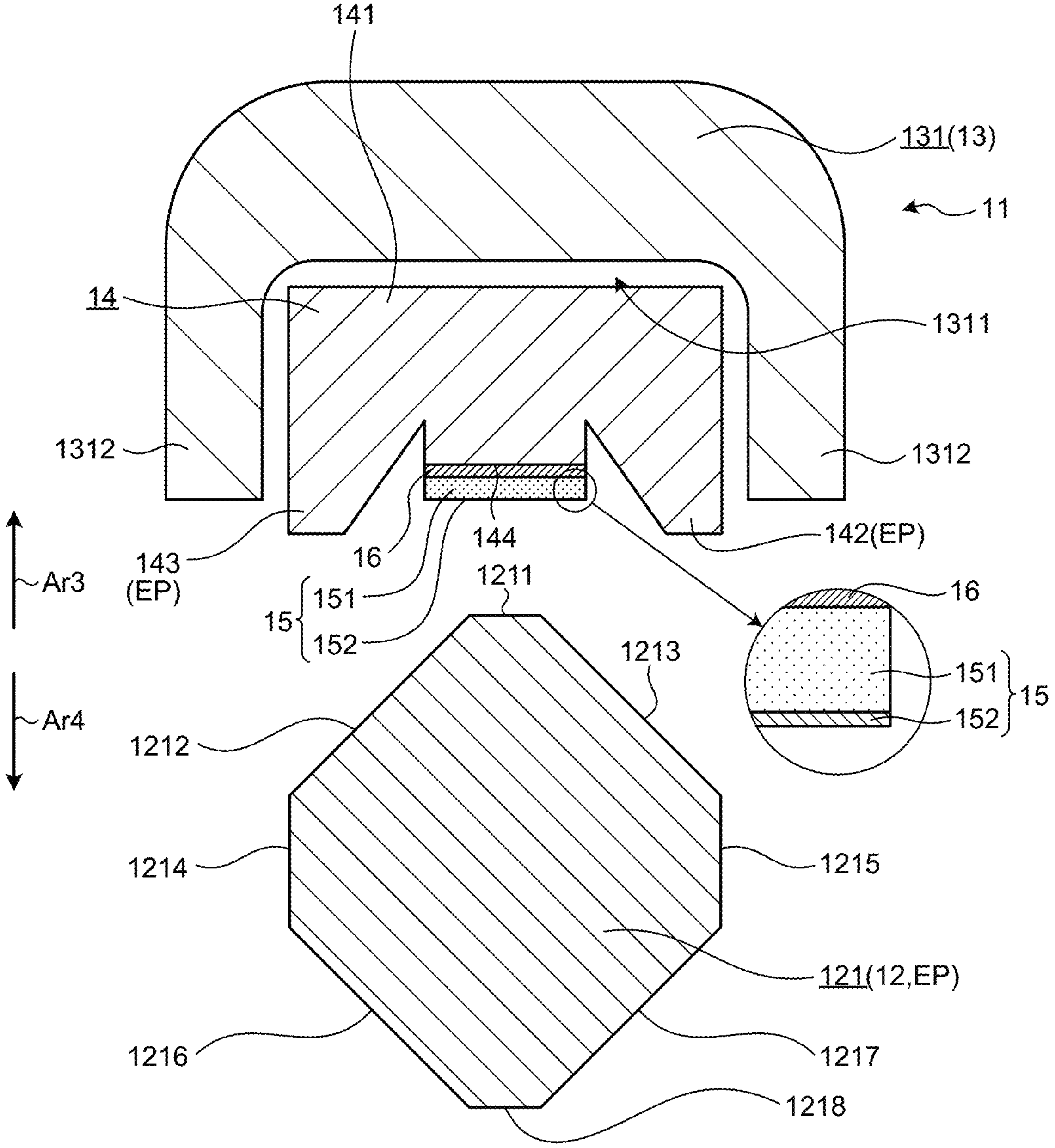
FIG. 3 is a diagram illustrating a configuration of a jaw and an ultrasound blade.

FIG. 3 is a diagram illustrating a configuration of the jaw 11 and the ultrasound blade 12. Specifically, FIG. 3 is a sectional view of the jaw 11 and the ultrasound blade 12 cut along a plane orthogonal to the central axis Ax1. For convenience of explanation, illustration of a cover RC has been omitted in FIG. 3.

For description of a configuration of the jaw 11 hereinafter, a direction separating from the treatment portion 121 will be referred to as a rearward direction Ar3 and a direction approaching the treatment portion 121 will be referred to as a treatment portion direction Ar4.

The jaw 11 may correspond to a grasping portion. This jaw 11 may be configured to be rotatable about a central axis of the first pin Pi1 (an axis along a direction orthogonal to the plane of paper of FIG. 1 or FIG. 2) by being pivotally supported about the first pin Pi1 at the end portion of the sheath 10, the end portion being in the distal direction Ar1. By rotating about the central axis of the first pin Pi1, the jaw 11 can be opened or closed relative to the treatment portion 121 provided at an end portion of the ultrasound blade 12, the end portion being in the distal direction Ar1. By the jaw 11 being closed relative to the treatment portion 121, a treatment target may be grasped between the jaw 11 and the treatment portion 121. This jaw 11 may include, as illustrated in FIG. 3, an arm 13 and a wiper jaw 14.

The arm 13 may be formed of an electrically conducting material. This arm 13 may be, as illustrated in FIG. 2 and FIG. 3, a portion having an arm main body 131 (FIG. 3) and a bearing portion 132 (FIG. 2) that have been formed integrally with each other.

The arm main body 131 may be formed of an approximately platy body that is elongated. In this embodiment, a longitudinal direction of the arm main body 131 can be a direction along a curve extending leftward in the distal direction Ar1 as viewed from the proximal direction Ar2 in a state where the jaw 11 has been positioned above the treatment portion 121.

As illustrated in FIG. 3, a recessed portion 1311 may be provided on a surface of this arm main body 131, the surface being in the treatment portion direction Ar4, the recessed portion 1311 extending from a proximal end of the arm main body 131 along the longitudinal direction in the distal direction Ar1.

A second pin Pi2 (FIG. 2) may extend in the width direction, may be cylindrical or substantially cylindrical and may be fixed by welding at a position located at an approximate center of a longitudinal length of the jaw 11. The position may be in side wall portions 1312 at both ends of a width of the arm main body 131, the side wall portions 1312 forming the recessed portion 1311.

Furthermore, the cover RC (FIG. 2 and FIG. 3) formed of an electrically insulating resin can be integrally formed on a surface of the arm main body 131, the surface being in the rearward direction Ar3, in a state where the surface in the rearward direction Ar3 is covered with the cover RC. In this embodiment, the cover RC may be formed on the arm main body 131 by insert molding but the disclosure is not limited to this embodiment. For example, in another adoptable configuration, the cover RC may be fixed to the arm main body 131 by snap fitting or use of a metal pin.

The bearing portion 132 may be provided at the proximal end of the arm main body 131 and pivotally supported on the sheath 10 by the first pin Pi1.

Furthermore, a third pin "Pi3" (FIG. 2) may be fixed to the bearing portion 132 by welding. The third pin Pi3 may extend in the width direction and may be cylindrical. This third pin Pi3 may be connected to an opening and closing mechanism "D1" (FIG. 2) inserted inside and through the sheath 10. In association with movement of the opening and closing mechanism D1 in the distal direction Ar1 or the proximal direction Ar2, the movement corresponding to opening or closing operation on the operation handle 7 by an operator, such as an operating surgeon, the jaw 11 can be rotated about the central axis of the first pin Pi1 to be opened or closed relatively to the treatment portion 121.

The wiper jaw 14 may be formed of an electrically conducting material, such as stainless steel or a titanium alloy, and has been attached to the arm 13. As illustrated in FIG. 3, this wiper jaw 14 may include a wiper jaw main body 141, plural first tooth portions 142, and plural second tooth portions 143.

The wiper jaw main body 141 may be formed of an elongated platy body extending along the longitudinal direction of the arm main body 131. Furthermore, the wiper jaw main body 141 may have an outer shape that has been set to be approximately the same as an inner shape of the recessed portion 1311. Inside the recessed portion 1311, the second pin Pi2 can penetrate the wiper jaw main body 141 along the width direction, and the wiper jaw main body 141 can be pivotally supported on the arm 13 such that the wiper jaw main body 141 is able to swing about a central axis (an axis along the width direction) of the second pin Pi2. That is, enabling the wiper jaw 14 to swing about the central axis of the second pin Pi2 allows a position to be located at the approximate center of the longitudinal length of the jaw 11, and not somewhere in the proximal direction Ar2 in the jaw 11. The position being where the strongest force is applied to a treatment target when the treatment target is grasped between the jaw 11 and the treatment portion 121. Force is thereby applied substantially evenly to the treatment target grasped between the jaw 11 and the treatment portion 121.

The plural first tooth portions 142 can each protrude in the treatment portion direction Ar4 from one end of a width of a surface of the wiper jaw main body 141, the surface being in the treatment portion direction Ar4, and can be arranged in parallel in a longitudinal direction of the wiper jaw main body 141.

The plural second tooth portions 143 can each protrude in the treatment portion direction Ar4 from the other end of the width of the surface of the wiper jaw main body 141. The surface can be in the treatment portion direction Ar4, and can be arranged in parallel in the longitudinal direction of the wiper jaw main body 141.

A center area (surface) 144 positioned between the plural first tooth portions 142 and the plural second tooth portions 143 may be located at the center of the width of the surface of the wiper jaw main body 141. The surface being in the treatment portion direction Ar4, maybe formed of a flat surface, as illustrated in FIG. 3. A pad 15 may be provided on the center area 144, as illustrated in FIG. 3. The center area 144 can be said as a middle surface or an intermediate surface.

A detailed configuration of the pad 15 will be described in a later section, "Configuration of Pad".

The ultrasound blade 12 may have an elongated shape and may be formed of an electrically conducting material. Furthermore, as illustrated in FIG. 2, the ultrasound blade 12 may be inserted inside and through the sheath 10 in a state where the treatment portion 121 can protrude outside. An end portion of the ultrasound blade 12, the end portion being in the proximal direction Ar2, may be mechanically connected to an ultrasound transducer 52 included in the ultrasound transducer unit 5, as illustrated in FIG. 1. The ultrasound blade 12 may transmit ultrasound vibration generated by the ultrasound transducer unit 5 from the end portion of the ultrasound blade 12, the end portion being in the proximal direction Ar2, to the treatment portion 121. In this embodiment, the ultrasound vibration can include longitudinal vibration that is vibration along the central axis Ax1.

In this embodiment, the treatment portion 121 may extend, similarly to the jaw 11, along a curve extending leftward in the distal direction Ar1 as viewed from the proximal direction Ar2, in a state where the jaw 11 has been positioned above the treatment portion 121. Furthermore, the treatment portion 121 may have, as illustrated in FIG. 3, an approximately octagon-shaped cross section cut along a plane orthogonal to the central axis Ax1. The octagonal shape of the cross section of the treatment portion 121 is just an example, and the cross section may have a circular shape or any other shape. For convenience of explanation, the cross section of the treatment portion 121 will be assumed to be octagon-shaped in the description hereinafter.

A flat surface of the treatment portion 121 may be positioned or located near the jaw 11 and will hereinafter be referred to as a first surface 1211. Furthermore, additional surfaces connected to the first surface 1211 along a circumferential direction around a central axis of the treatment portion 121 will be referred to as a second surface 1212 and a third surface 1213. Furthermore, surfaces respectively connected to the second and third surfaces 1212 and 1213 along the circumferential direction around the central axis of the treatment portion 121 will be referred to as a fourth surface 1214 and a fifth surface 1215. Furthermore, surfaces respectively connected to the fourth and fifth surfaces 1214 and 1215 along the circumferential direction around the central axis of the treatment portion 121 will be referred to as a sixth surface 1216 and a seventh surface 1217. Furthermore, a surface positioned between the sixth and seventh surfaces 1216 and 1217 and on one side opposite to a side where the first surface 1211 is will be referred to as an eighth surface 1218.

The ultrasound transducer unit 5 may include, as illustrated in FIG. 1, a transducer (TD) case 51 and the ultrasound transducer 52.

The TD case 51 may support the ultrasound transducer 52 and may be detachably connected to the holding case 6.

The ultrasound transducer 52 may generate ultrasound vibration, under control by the control device 3. In this embodiment, the ultrasound transducer 52 may be formed of a bolt-clamped Langevin transducer (BLT).

Configuration of Control Device

The control device 3 can integrally control operation of the ultrasound treatment tool 2 through an electric cable C (FIG. 1).

Specifically, the control device 3 may detect treatment operation on the switches 8 by an operator, such as an operating surgeon, through the electric cable C. In a case where the control device 3 detects the treatment operation, the control device 3 can apply, through the electric cable C, treatment energy to a treatment target grasped between the jaw 11 and the treatment portion 121. That is, the control device 3 can implement treatment of the treatment target.

For example, in applying ultrasound energy to a treatment target, the control device 3 may supply drive power to the ultrasound transducer 52 through the electric cable C. The ultrasound transducer 52 thereby generates longitudinal vibration (ultrasound vibration) that is vibration along the central axis Ax. Furthermore, the treatment portion 121 can be vibrated at a desired amplitude by the longitudinal vibration. The ultrasound vibration may then be applied from the treatment portion 121 to the treatment target grasped between the jaw 11 (the pad 15) and the treatment portion 121. In other words, ultrasound energy can be applied to the treatment target from the treatment portion 121.

Furthermore, for application of high frequency energy to a treatment target, the control device 3 may supply high frequency electric power between the jaw 11 and the ultrasound blade 12, through the electric cable C. In response to application of the high frequency electric power between the jaw 11 and the ultrasound blade 12, high frequency electric current can flow to the treatment target positioned between the plural first and second tooth portions 142 and 143 and the treatment portion 121. In other words, high frequency energy can be applied to the treatment target.

As described above, the treatment portion 121 and the plural first and second tooth portions 142 and 143 of the wiper jaw 14 can each function as an electrode EP (FIG. 3) that can allow high frequency electric current to flow between the treatment portion 121 and the plural first and second tooth portions 142 and 143 (treatment target).

In this embodiment, the treatment portion 121 and the plural first and second tooth portions 142 and 143 can each function as the electrode EP but the disclosure is not limited to this embodiment. For example, a so-called monopolar structure, in which only the treatment portion 121 or the plural first and second tooth portions 142 and 143 functions/function as an electrode EP or electrodes EP, or a structure, in which two bipolar electrodes EP are provided in only the wiper jaw 14 of the treatment portion 121 and the wiper jaw 14, may be adopted instead.

Configuration of Pad

The pad 15 may be a portion (surface) that comes into contact with the treatment portion 121 when the jaw 11 may be brought close to the treatment portion 121 and may correspond to a contact portion (contact surface). The pad 15 may include, as illustrated in FIG. 3, a first resin portion 151 and a second resin portion 152.

The first resin portion 151 may be formed of a first resin that is electrically insulating and biocompatible, may be a coating formed by a publicly known coating process including coating, and may correspond to a resin layer. In this embodiment, polytetrafluoroethylene (PTFE) may be adopted as the first resin. Without being limited to PTFE, a resin, such as polybenzimidazol (PBI) having a low friction coefficient, may be adopted as the first resin. Furthermore, a surface of the first resin portion 151, the surface being in the treatment portion direction Ar4, may be formed as a flat surface that follows the center area 144.

The second resin portion 152 may include a mixed resin that is electrically insulating and biocompatible, may be a coating layered over the first resin portion 151 by a publicly known coating process including coating, and may correspond to a resin layer. That is, the second resin portion 152 may be positioned on one side of the first resin portion 151, the one side being toward the treatment portion 121. In this embodiment, a resin adopted as the mixed resin may include a resin having an ether group and a ketone group, for example, polyetheretherketone (PEEK), mixed in PTFE. That is, a resin having an ether group and a ketone group, for example, PEEK, may correspond to a second resin. Without being limited to PEEK, a resin, such as polyetherketone (PEK) or polyetherketoneetherketoneketone (PEKEKK), having excellent abrasion resistance and heat resistance may be adopted as the second resin. The friction coefficient of the first resin may be lower than that of the second resin. Furthermore, the second resin may be higher in abrasion resistance than the first resin. That is, the pad 15 may be formed of a low-friction material. However, another resin (the second resin) can be mixed in consideration of influences, such as damage to the ultrasound blade 12 and high temperatures that are reached, in order to improve resistance (in particular, abrasion resistance). Furthermore, a surface of the second resin portion 152, the surface being in the treatment portion direction Ar4, may be formed as or including a flat surface that follows the center area 144. The flat surfaces of the pad 15 and the first surface 1211 can come into contact with each other when the jaw 11 is brought close to the treatment portion 121.

The first resin portion 151 may have a thickness dimension of 5 μm or more and 500 μm or less.

The second resin portion 152, on the other hand, may have a thickness dimension of 5 μm or more and 15 μm or less. Furthermore, the thickness dimension of the second resin portion 152 may be 1/20 or more and 3/20 or less of the total thickness dimension of the pad 15 including the first and second resin portions 151 and 152. For example, in a case where the total thickness dimension of the pad 15 is 100 μm, the thickness dimension of the second resin portion 152 is set to 5 μm (100 μm/20) or more and 15 μm (100 μm×3/20) or less.

Furthermore, a volume ratio of PEEK mixed in the mixed resin forming the second resin portion 152 to PTFE may be 20% or more and 65% or less.

In a case where the pad 15 that is a coating is formed on the center area 144 of the wiper jaw 14 formed of a metal, there may be a sticking force between the pad 15 and the center area 144.

In this embodiment, in consideration of the above mentioned sticking force, as illustrated in FIG. 3, a plating layer 16 may be provided between the center area 144 and the pad 15.

The plating layer 16 may be eutectic plating including a resin component that may be the same as a resin included in the pad 15. In this embodiment, the plating layer 16 may be Ni-PTFE plating. In a state where the pad 15 has been provided on the plating layer 16, the resin component included in the plating layer 16 and the resin included in the pad 15 can be fused together.

The plating layer 16 may have a thickness dimension of, for example, 1 μm or more and 100 μm or less. Furthermore, a percentage of the resin component (PTFE) included in the plating layer 16 may be 30% or more for maintaining sticking force between the plating layer 16 and the pad 15. Furthermore, the percentage of the resin component (PTFE) included in the plating layer 16 may be 95% or less for maintaining strength of the plating layer 16.

Abrasion Resistance and Heat Resistance of Pad

PTFE has a heat insulating function. Therefore, in a case where the pad 15 is formed of PTFE as a structural body, the thickness dimension of the pad 15 may be increased and frictional heat generated in the pad 15 by application of ultrasound vibration can stay in the pad 15. As a result, the pad 15 may be deteriorated by the frictional heat.

Therefore, in terms of heat resistance to the frictional heat, the pad 15 can be formed of a coating having a small thickness dimension and reduced in heat insulation performance, so that the frictional heat generated in the pad 15 can be quickly transmitted from the pad 15 to the wiper jaw 14.

However, PTFE has a property of being easily abraded away at about 150° C. That is, if the thickness dimension of the pad 15 is decreased in terms of heat resistance to improve heat radiation, application of ultrasound vibration can cause powder (hereinafter, referred to as abrasion powder) to be generated from the pad 15 by abrasion.

Therefore, in terms of abrasion resistance to ultrasound vibration, the mixed resin that is obtained by mixing the second resin such as PEEK into PTFE can be used as a material forming the pad 15, the second resin having excellent abrasion resistance.

The applicant has verified, by a first experiment described below, which position in the pad 15 is the best position to use the mixed resin.

In the first experiment, the same ultrasound vibration was applied from the treatment portion 121 to pad samples No. 1 to No. 7 described below. In the first experiment, a time period (a resistant time period) up to breakage of each of the pad samples, the pad 15, by frictional heat due to the ultrasound vibration and a time period (a powder generation time period) up to generation of abrasion powder at the pad sample, the pad 15, due to the ultrasound vibration were measured.

The total thickness dimension of each of the pad samples No. 1 to No. 7, the pad 15, was 100 μm. Furthermore, a base layer referred to hereinafter is a layer positioned in the rearward direction Ar3 the most. Furthermore, a surface layer referred to hereinafter is a layer positioned in the treatment portion direction Ar4 the most. Furthermore, an intermediate layer referred to hereinafter is a layer positioned between the base layer and the surface layer. The base layer, the intermediate layer, and the surface layer all have the same thickness dimension.

Specifically, the pad sample No. 1 is a sample having a base layer formed of PTFE, and an intermediate layer and a surface layer each formed of a mixed resin having PEEK mixed, at a volume ratio of 35%, in PTFE.

The pad sample No. 2 is a sample having a base layer and an intermediate layer each formed of PTFE, and a surface layer formed of a mixed resin having PEEK mixed, at a volume ratio of 35%, in PTFE.

The pad sample No. 3 is a sample having a base layer formed of PTFE, an intermediate layer formed of a mixed resin having PEEK mixed, at a volume ratio of 15%, in PTFE, and a surface layer formed of a mixed resin having PEEK mixed, at a volume ratio of 35%, in PTFE.

The pad sample No. 4 is a sample having a base layer and a surface layer each formed of PTFE, and an intermediate layer formed of a mixed resin having PEEK mixed, at a volume ratio of 35%, in PTFE.

The pad sample No. 5 is a sample having a base layer and a surface layer each formed of a mixed resin having PEEK mixed, at a volume ratio of 15%, in PTFE, and an intermediate layer formed of a mixed resin having PEEK mixed, at a volume ratio of 35%, in PTFE.

The pad sample No. 6 is a sample having a base layer formed of a mixed resin having PEEK mixed, at a volume ratio of 35%, in PTFE, and an intermediate layer and a surface layer each formed of PTFE.

The pad sample No. 7 is a sample having a base layer formed of a mixed resin having PEEK mixed, at a volume ratio of 35%, in PTFE, an intermediate layer formed of a mixed resin having PEEK mixed, at a volume ratio of 15%, in PTFE, and a surface layer formed of PTFE.

Results of the first experiment are listed in Table 1 below. In Table 1, "not adoptable", "same as conventional product", "improved", and "largely improved" written for resistant time periods and powder generation time periods indicate results of relative evaluation of the corresponding time periods. "Not adoptable" indicates a level that is unable to be adopted as a product. "Same as conventional product" indicates a level equivalent to that of a conventional product. "Improved" indicates a level that has been improved from that of the conventional product. "Largely improved" indicates a level that has been largely improved from that of the conventional product.

TABLE 1

| Pad sample | Base layer | Intermediate layer | Surface layer | Resistant time period | Powder generation time period |
|---|---|---|---|---|---|
| No. 1 | PTFE | 35% PEEK | 35% PEEK | Improved | Improved |
| No. 2 | PTFE | PTFE | 35% PEEK | Largely improved | Improved |
| No. 3 | PTFE | 15% PEEK | 35% PEEK | Improved | Improved |
| No. 4 | PTFE | 35% PEEK | PTFE | Improved | Not adoptable |
| No. 5 | 15% PEEK | 35% PEEK | 15% PEEK | Improved | Improved |
| No. 6 | 35% PEEK | PTFE | PTFE | Improved | Same as conventional product |
| No. 7 | 35% PEEK | 15% PEEK | PTFE | Improved | Not adoptable |

As to the results of the first experiment, the optimum position to use the mixed resin in the pad 15 was found to be the surface layer, as can be seen from comparison between the pad samples No. 1 to No. 3 and the pad samples No. 4 to No. 7. Furthermore, comparison between the pad sample No. 1 and the pad sample No. 2 indicates that the pad sample No. 2 had better results, and the thickness dimension of the layer using the mixed resin was found to be smaller than the layers formed of PTFE.

The applicant has also verified, by a second experiment described below, the optimum thickness dimension of the surface layer using the mixed resin and the optimum volume ratio of PEEK to be mixed in the mixed resin to PTFE therein.

The second experiment was an experiment similar to the above described first experiment and was performed for pad samples No. 8 to No. 20 described below.

The total thickness dimension of each of the pad samples No. 8 to No. 20, the pad 15, was 100 μm, similarly to the pad samples No. 1 to No. 7 described above. Furthermore, the layers other than the surface layer of each of the pad samples No. 8 to No. 20, the pad 15, were formed of PTFE. Furthermore, firing temperatures for formation of the surface layers of the pad samples No. 8 to No. 20 were all 375° C. As a result of performing the first experiment for each sample made at each of firing temperatures of 420° C., 390° C., and 375° C., good results were obtained in terms of resistant time periods and powder generation time periods for 375° C., and the firing temperature for formation of the surface layers of the pad samples No. 8 to No. 20 was thus also set to 375° C., although specific description of those results will be omitted.

Specifically, the pad sample No. 8 is a sample having: a surface layer formed of a mixed resin having PEEK mixed, at a volume ratio of 25%, in PTFE; and 10 μm as the thickness dimension of the surface layer.

The pad sample No. 9 is a sample having; a surface layer formed of a mixed resin having PEEK mixed, at a volume ratio of 35%, in PTFE; and 10 μm as the thickness dimension of the surface layer.

The pad sample No. 10 is a sample having: a surface layer formed of a mixed resin having PEEK mixed, at a volume ratio of 45%, in PTFE; and 10 μm as the thickness dimension of the surface layer.

The pad sample No. 11 is a sample having: a surface layer formed of a mixed resin having PEEK mixed, at a volume ratio of 25%, in PTFE; and 15 μm as the thickness dimension of the surface layer.

The pad sample No. 12 is a sample having: a surface layer formed of a mixed resin having PEEK mixed, at a volume ratio of 35%, in PTFE; and 15 μm as the thickness dimension of the surface layer.

The pad sample No. 13 is a sample having: a surface layer formed of a mixed resin having PEEK mixed, at a volume ratio of 45%, in PTFE; and 15 μm as the thickness dimension of the surface layer.

The pad sample No. 14 is a sample having: a surface layer formed of a mixed resin having PEEK mixed, at a volume ratio of 25%, in PTFE; and 20 μm as the thickness dimension of the surface layer.

The pad sample No. 15 is a sample having: a surface layer formed of a mixed resin having PEEK mixed, at a volume ratio of 35%, in PTFE; and 20 μm as the thickness dimension of the surface layer.

The pad sample No. 16 is a sample having: a surface layer formed of a mixed resin having PEEK mixed, at a volume ratio of 45%, in PTFE; and 20 μm as the thickness dimension of the surface layer.

The pad sample No. 17 is a sample having: a surface layer formed of a mixed resin having PEEK mixed, at a volume ratio of 25%, in PTFE; and 25 μm as the thickness dimension of the surface layer.

The pad sample No. 18 is a sample having: a surface layer formed of a mixed resin having PEEK mixed, at a volume ratio of 35%, in PTFE; and 25 μm as the thickness dimension of the surface layer.

The pad sample No. 19 is a sample having: a surface layer formed of a mixed resin having PEEK mixed, at a volume ratio of 45%, in PTFE; and 25 μm as the thickness dimension of the surface layer.

The pad sample No. 20 is a sample having: a surface layer formed of PEEK; and 5 μm as the thickness dimension of the surface layer.

Results of the second experiment are listed in Table 2 below. In Table 2, "not adoptable", "same as conventional product", "improved", and "largely improved" written for resistant time periods and powder generation time periods indicate levels equivalent to those in Table 1.

TABLE 2

| Pad sample | Surface layer [μm] | Concentration of PEEK [%] | Resistant time period | Powder generation time period |
|---|---|---|---|---|
| No. 8 | 10 | 25 | Largely improved | Same as conventional product |
| No. 9 | 10 | 35 | Improved | Largely improved |
| No. 10 | 10 | 45 | Largely improved | Largely improved |
| No. 11 | 15 | 25 | Improved | Not adoptable |
| No. 12 | 15 | 35 | Largely improved | Largely improved |
| No. 13 | 15 | 45 | Largely improved | Largely improved |
| No. 14 | 20 | 25 | Improved | Same as conventional product |

TABLE 2-continued

| Pad sample | Surface layer [μm] | Concentration of PEEK [%] | Resistant time period | Powder generation time period |
|---|---|---|---|---|
| No. 15 | 20 | 35 | Largely improved | Improved |
| No. 16 | 20 | 45 | Largely improved | Not adoptable |
| No. 17 | 25 | 25 | Improved | Not adoptable |
| No. 18 | 25 | 35 | Largely improved | Same as conventional product |
| No. 19 | 25 | 45 | Largely improved | Largely improved |
| No. 20 | 5 | 100 | Improved | Not adoptable |

As to the results of the second experiment, from results of pad samples having the same thickness dimension, the higher the concentration of PEEK is, the more improved the resistant time period tends to be. Furthermore, when the thickness dimension is 10 μm and 15 μm, the higher the concentration of PEEK is, the more improved the powder generation time period tends to be. Furthermore, from results of pad samples having the same PEEK concentration, the smaller the thickness dimension is, the more improved the resistant time period and powder generation time period tend to be.

The overall results for the pad samples No. 8 to No. 20 indicate that the resistant time periods and powder generation time periods for the pad sample No. 10 and the pad sample No. 13 were improved.

Figure 4:
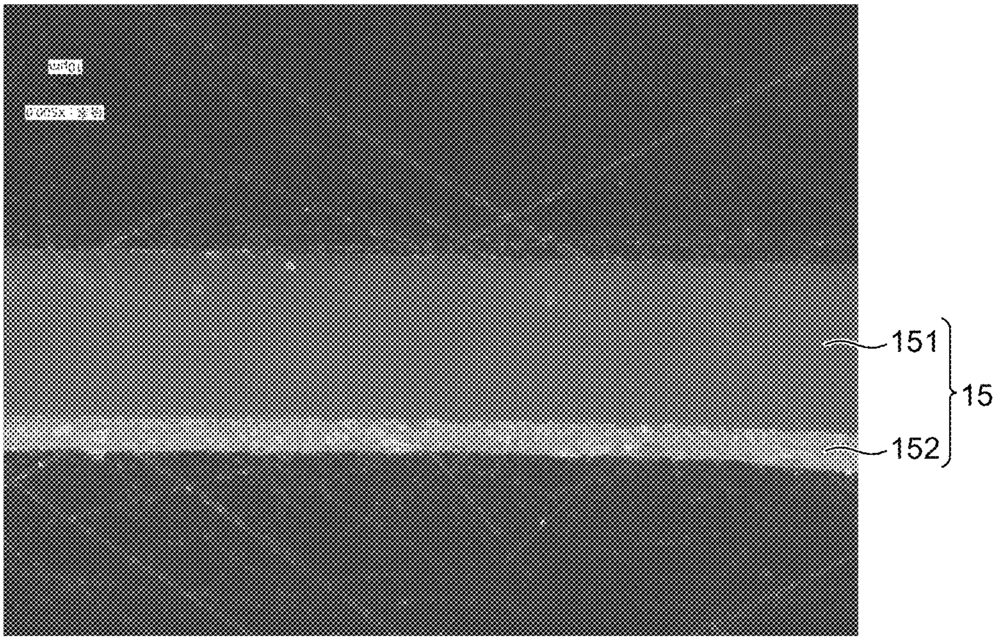
FIG. 4 is an image of a cross section of a pad sample No. 9 observed by means of an optical microscope.
Figure 5:
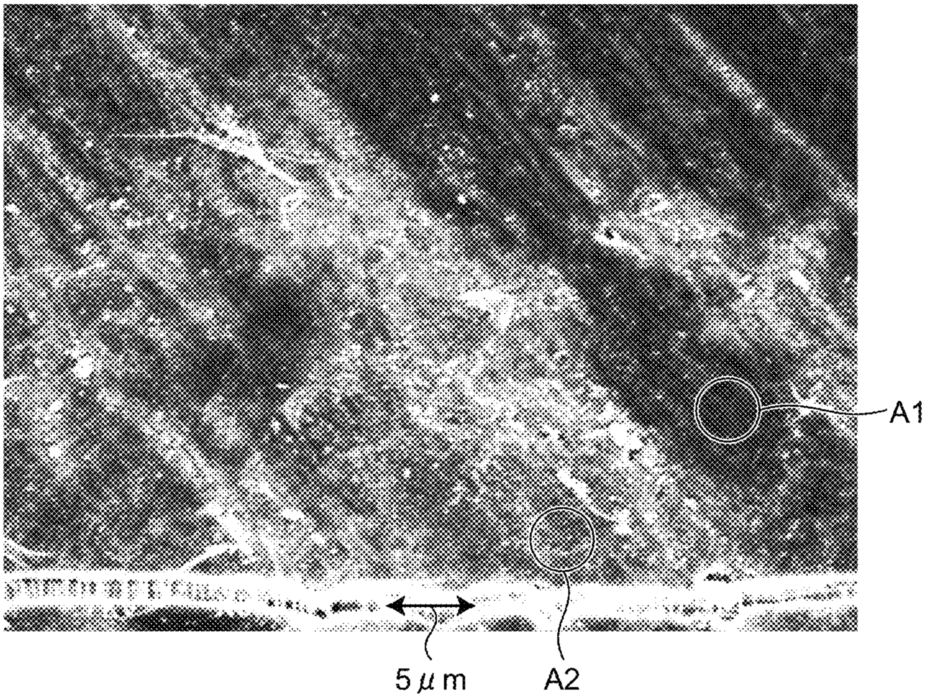
FIG. 5 is an image of a surface layer (a second resin portion) of the pad sample No. 9 observed by means of an electron microscope (scanning electron microscopy (SEM)).

FIG. 4 is an image of a cross section of the pad sample No. 9 observed by means of an optical microscope. FIG. 5 is an image of the surface layer (second resin portion 152) of the pad sample No. 9 observed by means of an electron microscope (scanning electron microscopy (SEM)).

The surface layer (second resin portion 152) may be formed by firing at 375° C. after application of the mixed resin onto the first resin portion (first resin layer) 151, the mixed resin having nano particles of PTFE and particles of PEEK (of about 10 μm) mixed together. In FIG. 5, portions illustrated in black correspond to PTFE. Furthermore, portions illustrated in white correspond to PEEK. An area A1 where PTFE is dominantly present and an area A2 where PEEK is partly mixed at the nanoscale level in PTFE are present in the surface layer, as illustrated in FIG. 5.

The above described embodiment has the following effects.

The pad 15 in the ultrasound treatment tool 2 according to the embodiment can include the first resin portion 151 formed of the first resin and the second resin portion (second resin layer) 152 layered over the first resin portion 151 and formed of the mixed resin having the second resin mixed in the first resin. The first resin may be formed of PTFE. Furthermore, the second resin may be formed of PEEK. As can been seen from FIG. 5, PEEK has been dispersed at the nanoscale level and the structure has been reinforced by the uneven dispersion (matrix structure) of such PEEK.

Therefore, the ultrasound treatment tool 2 according to the embodiment includes the pad 15 having excellent abrasion resistance and can enable a structure to be provided, the structure having the pad 15 difficult to be deteriorated by abrasion even if ultrasound vibration is provided from the treatment portion 121.

In particular, the pad 15 may be formed of a coating. Therefore, the pad 15 may be able to be provided in a state of being stuck to the center area 144 of the wiper jaw 14.

That is, a structure is able to be provided, the structure allowing heat resistance between the center area 144 and the pad 15 to be reduced and facilitating quick transmission, from the pad 15 to the wiper jaw 14, of frictional heat generated in the pad 15 due to application of ultrasound vibration. Furthermore, because the pad 15 is able to be made very thin as compared with a conventional pad formed of a structural body, the frictional heat can be prevented from staying in the pad 15. Therefore, the pad 15 may have excellent heat resistance and the structure including the pad 15 can be difficult deteriorate by frictional heat.

Furthermore, the thickness dimension of the second resin portion 152 may be smaller than that of the first resin portion 151, in the ultrasound treatment tool 2 according to the embodiment. As can be seen from the results of the first experiment for the pad sample No. 1 and pad sample No. 2, making the thickness dimension of the second resin portion 152 smaller than that of the first resin portion 151 enables formation of the pad 15 having excellent abrasion resistance and heat resistance.

In particular, the thickness dimension of the second resin portion 152 may be 5 μm or more and 1/20 or more of the total thickness dimension including the first and second resin portions 151 and 152. Therefore, if the thickness dimension of the second resin portion 152 is too small, improvement of the abrasion resistance of the pad 15 by the mixing of PEEK is difficult to be achieved, and having the above described thickness dimension enables the pad 15 to be improved in abrasion resistance.

Furthermore, the thickness dimension of the second resin portion 152 may be 15 μm or less and 3/20 or less of the total thickness dimension including the first and second resin portions 151 and 152. Some of the pad samples No. 14 to No. 19 each have the second resin portion 152 with a thickness dimension exceeding 20 μm. Therefore, the improvement of the abrasion resistance of the pad 15 due to the mixing of PEEK is achieved.

Furthermore, the volume ratio of PEEK mixed in the second resin portion 152 (mixed resin) to PTFE may be 20% or more. Therefore, in a case where the volume ratio of PEEK mixed therein is less than 20%, PEEK portions mixed in PTFE may not bond to each other and the structural reinforcement by PEEK can be insufficient, and having the above described mixing ratio instead may enable sufficient structural reinforcement by PEEK and sufficient improvement of the abrasion resistance of the pad 15.

Furthermore, the volume ratio of PEEK mixed in the second resin portion 152 (mixed resin) to PTFE may be 65% or less. Therefore, in a case where the volume ratio of PEEK mixed therein exceeds 65%, properties of PEEK can be increased and heat resistance can be thus reduced, and having the above described mixing ratio instead may enable improvement of the heat resistance of the pad 15.

Furthermore, the thickness dimension of the first resin portion 151 may be 5 μm or more. Therefore, in a case where the thickness dimension of the first resin portion 151 is 5 μm or less, electric insulation provided by the pad 15 may be difficult to be maintained, and having the above described thickness dimension instead may enable electric insulation of the pad 15 to be maintained.

Furthermore, the thickness dimension of the first resin portion 151 may be 500 μm or less. Therefore, in a case where the thickness dimension of the first resin portion 151 exceeds 500 μm, the pad 15 can be structured such that frictional heat tends to stay in the pad 15, but having the above described thickness dimension instead enables the pad 15 to be structured such that frictional heat is difficult to stay in the pad 15 and the pad 15 is difficult to be deteriorated by the frictional heat.

Furthermore, the above described plating layer 16 may be provided between the center area 144 and the pad 15, in the ultrasound treatment tool 2 according to the embodiment. Therefore, the sticking force of the pad 15 relative to the jaw 11 is able to be improved.

Other Embodiments

A mode for implementing the disclosure has been described thus far, but the disclosure should not be limited only to the embodiment described above.

First to fourth modified examples described hereinafter may also be adopted.

First Modified Example

Figure 6:
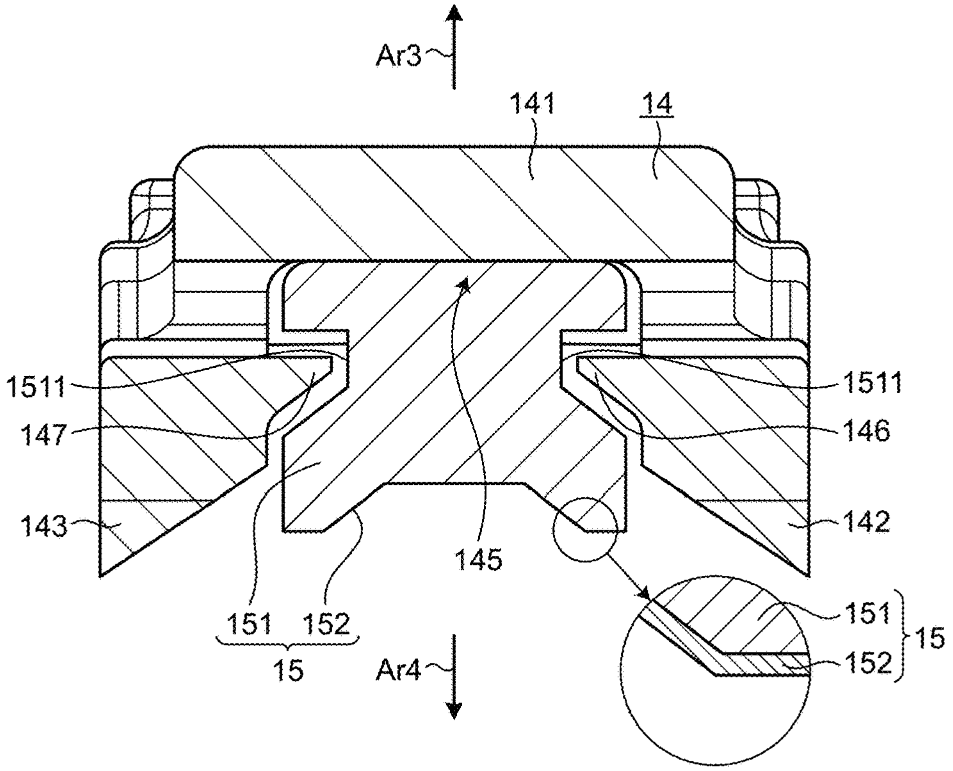
FIG. 6 is a diagram illustrating a first modified example of the embodiment.

FIG. 6 is a diagram illustrating the first modified example of the embodiment. Specifically, FIG. 6 is a sectional view corresponding to FIG. 3. For convenience of explanation, illustration of a cover RC, an arm 13, and a treatment portion 121 has been omitted in FIG. 6.

In the above described embodiment, the first resin portion 151 may be, instead of a coating, a structural body like in this first modified example illustrated in FIG. 6.

As illustrated in FIG. 6, a wiper jaw 14 according to the first modified example may include a recessed portion 145 provided in part of a surface a wiper jaw main body 141. The surface may be in the treatment portion direction Ar4, the part may be at the center of a width of the wiper jaw 14 and may be positioned between plural first tooth portions 142 and plural second tooth portions 143. The recessed portion 145 may be recessed in the rearward direction Ar3 and extending along a longitudinal direction of the wiper jaw main body 141.

Furthermore, as illustrated in FIG. 6, side wall portions of the wiper jaw 14 may include claw portions 146 and 147 respectively provided to protrude toward the center of the width and extend along the longitudinal direction of the wiper jaw main body 141, the side wall portions may form the recessed portion 145 and be located at both ends of the width of the wiper jaw 14.

As illustrated in FIG. 6, a first resin portion 151 according to the first modified example may include, provided therein, groove portions 1511 respectively corresponding to the claw portions 146 and 147. A pad 15 according to this first modified example may be mechanically fixed to the wiper jaw 14 by the claw portions 146 and 147 respectively entering the groove portions 1511 and may be locked by the claw portions 146 and 147. That is, the plating layer 16 is not used. The first resin portion 151 may be formed by insert molding in the wiper jaw 14.

In the case where the above described structure according to the first modified example is adopted also, effects similar to those of the embodiment described above may be achieved.

Second Modified Example

Figure 7:
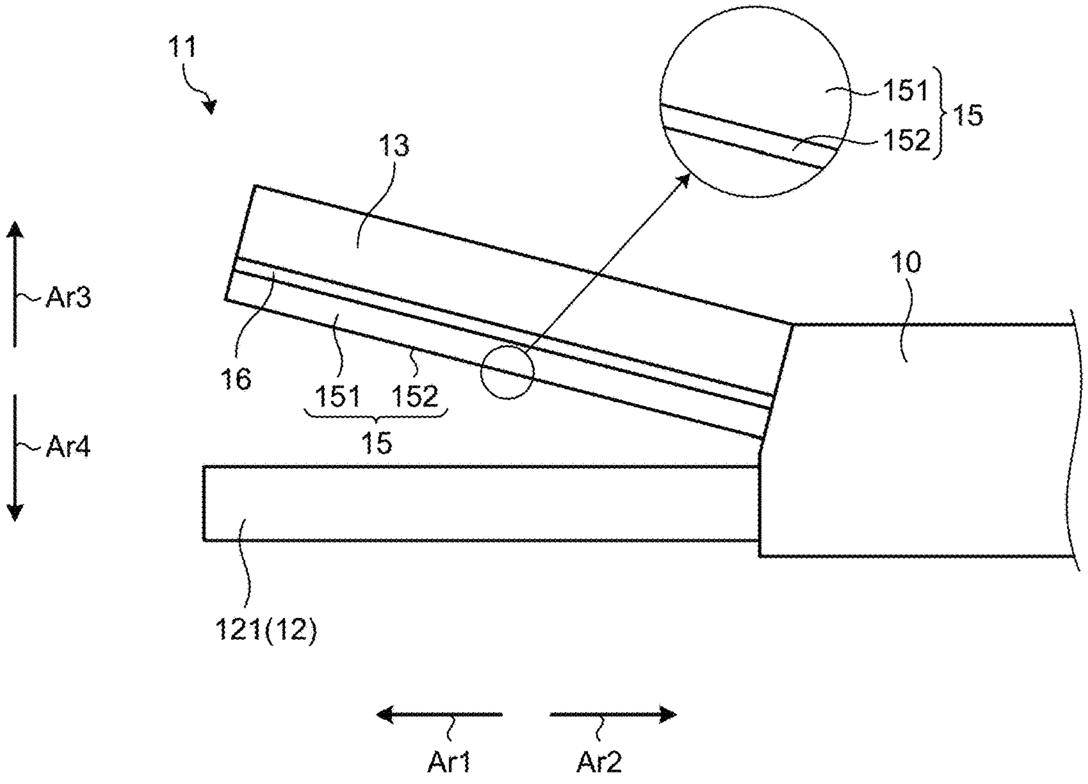
FIG. 7 is a diagram illustrating a second modified example of the embodiment.

FIG. 7 is a diagram illustrating the second modified example of the embodiment. Specifically, FIG. 7 is a diagram of a distal end portion of an ultrasound treatment tool 2 as viewed along the width direction. For convenience of explanation, illustration of a cover RC has been omitted in FIG. 7.

In the above described embodiment, the configuration including the arm 13 and the wiper jaw 14 that has been attached, to be swingable, to the arm 13 can be adopted as the grasping portion, but the grasping portion is not limited to this configuration. Any configuration without the wiper jaw 14 and capable of being opened and closed relative to the treatment portion 121 may be adopted as the grasping portion. That is, as illustrated in FIG. 7, a plating layer 16 and a pad 15 may be provided on a surface of an arm 13, the surface being in the treatment portion direction Ar4.

In the case where the above described structure according to the second modified example is adopted also, effects similar to those of the embodiment described above may be achieved.

A configuration without the wiper jaw 14 may be adopted similarly in the above described first modified example. That is, in the above described first modified example, the first resin portion 151 formed as a structural body can then be fixed to the arm 13.

Third Modified Example

Figure 8:
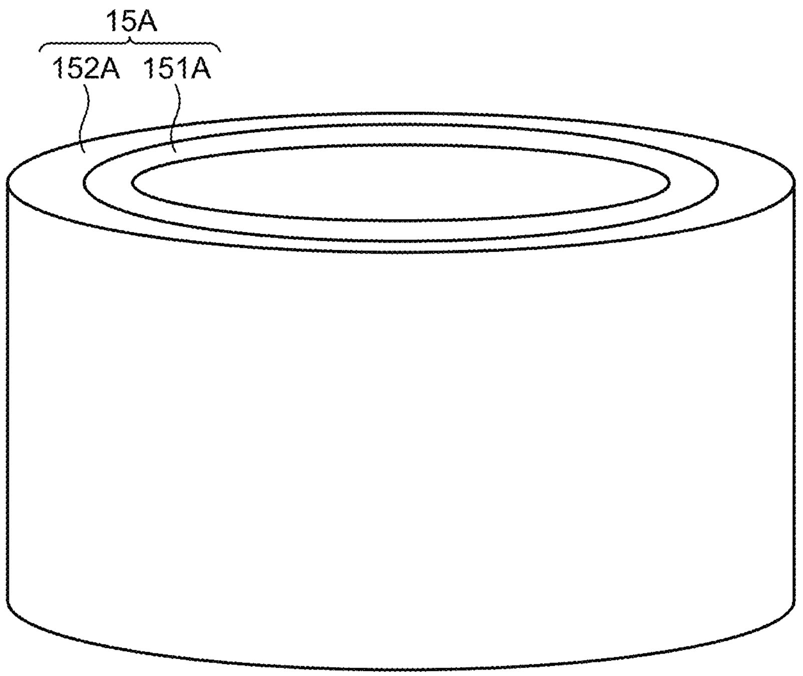
FIG. 8 is a diagram illustrating a third modified example of the embodiment.

FIG. 8 is a diagram illustrating the third modified example of the embodiment. Specifically, FIG. 8 is a perspective view of part of a tube 15A.

The tube 15A may be any of flexible medical tubes and medical pipes including catheters, liquid feeding tubes, gas feeding tubes, covering tubes for endoscopes, and endoscope channel tubes, and may correspond to a medical resin portion. The tube 15A may include, as illustrated in FIG. 8, a first resin portion 151A and a second resin portion 152A.

The first resin portion 151A may be a structural body having a tubular shape. The same material as the first resin portion 151 described above with respect to the embodiment may be adopted as a material for the first resin portion 151A.

The second resin portion 152A may be provided on an outer peripheral surface of the first resin portion 151A. The same material as the second resin portion 152 described above with respect to the embodiment may be adopted as a material for the second resin portion 152A. Furthermore, the second resin portion 152A may be a structural body or a coating.

The above described third modified example can enable formation of the tube 15A having excellent abrasion resistance and heat resistance.

Fourth Modified Example

Figure 9:
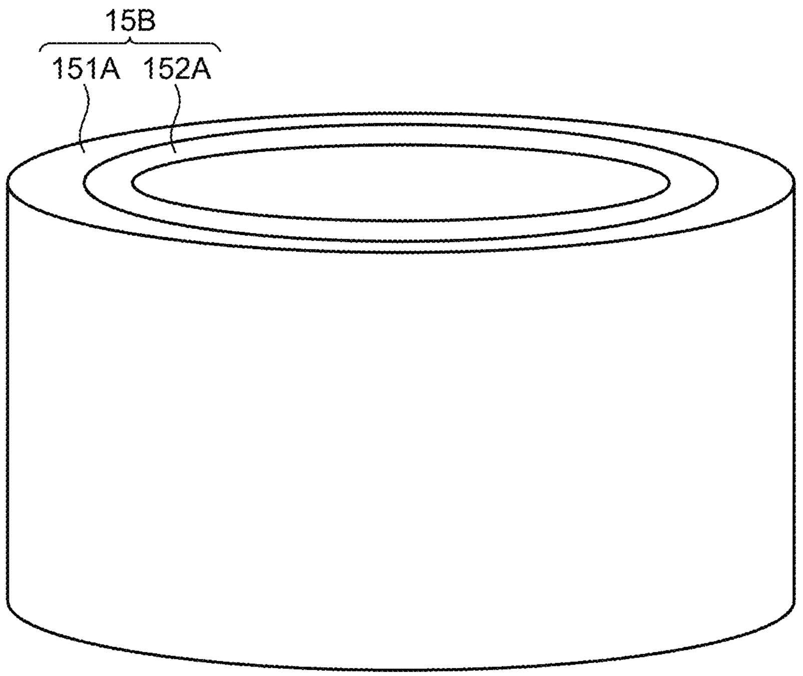
FIG. 9 is a diagram illustrating a fourth modified example of the embodiment.

FIG. 9 is a diagram illustrating the fourth modified example of the embodiment. Specifically, FIG. 9 is a perspective view of part of a tube 15B.

As illustrated in FIG. 9, the tube 15B may be different from the tube 15A described above with respect to the third modified example in that a second resin portion 152A may be provided on an inner peripheral surface of a first resin portion 151A.

In the case where the above described structure according to the fourth modified example is adopted also, effects similar to those of the third modified example described above may be achieved.

The following configuration also belongs to the technical scope of the present disclosure.

(1) A medical resin portion, including:

a first resin portion formed of a first resin that is biocompatible; and a second resin portion formed of a mixed resin that is obtained a second resin into a first resin, the second resin being biocompatible, wherein the second resin portion includes:

a portion where the first resin is dominantly present; and a portion where the second resin is mixed and present, at a nanoscale level, in the first resin.

The disclosure enables provision of an ultrasound treatment tool including a contact portion having excellent abrasion resistance.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. An ultrasound treatment tool, comprising:
- an ultrasound blade including a treatment portion located at a distal end of the ultrasound blade; and
- a jaw configured to open and close relative to the treatment portion, the jaw including:
  - a surface; and
  - a contact surface facing the ultrasound blade, the contact surface configured to be in contact with the treatment portion when the jaw is closed relative to the treatment portion, wherein the contact surface comprises:
    - a first resin layer positioned on the surface, the first resin layer formed of a first resin; and
    - a second resin layer layered over the first resin layer, the second resin layer formed of a mixed resin, the mixed resin being a mixture of a second resin and the first resin, wherein:
      - the first resin layer has a first thickness;
      - the second resin layer has a second thickness;
      - the second thickness is smaller than the first thickness;
      - the first resin has a first friction coefficient;
      - the second resin has a second friction coefficient;
      - the first friction coefficient is lower than the second friction coefficient;
      - the first resin has a first abrasion resistance;
      - the second resin has a second abrasion resistance; and
      - the second abrasion resistance is higher than the first abrasion resistance.

2. The ultrasound treatment tool according to claim 1, wherein a thickness of the second resin layer is 5 μm or more and 15 μm or less.

3. The ultrasound treatment tool according to claim 2, wherein a thickness of the first resin layer is 5 μm or more and 500 μm or less.

4. The ultrasound treatment tool according to claim 1, wherein;
- a total thickness value is a sum of a value of the first thickness and a value of the second thickness; and
- the second thickness is $\frac{1}{20}$ of the total thickness value or more and $\frac{3}{20}$ of the total thickness value or less.

5. The ultrasound treatment tool according to claim 1, wherein the first resin is polytetrafluoroethylene (PTFE).

6. The ultrasound treatment tool according to claim 5, wherein the second resin is a resin having an ether group and a ketone group.

7. The ultrasound treatment tool according to claim 6, wherein the second resin is polyetheretherketone (PEEK).

8. The ultrasound treatment tool according to claim 6, wherein a volume ratio of the mixed resin is a mixing ratio of the second resin relative to the first resin, the volume ratio of the second resin is 20% or more and 65% or less.

9. The ultrasound treatment tool according to claim 1, wherein at least one of the jaw and the treatment portion comprises an electrode configured to flow high frequency electric current.

10. The ultrasound treatment tool according to claim 9, wherein both the jaw and the treatment portion comprises the electrode.

11. The ultrasound treatment tool according to claim 1, wherein the contact surface is formed of a coating, and wherein the coating includes the first resin layer and the second resin layer.

12. The ultrasound treatment tool according to claim 11, wherein a plating layer is located between the surface and the contact surface.

13. An ultrasound treatment tool, comprising:
- an ultrasound blade including a treatment portion located at a distal end of the ultrasound blade; and
- a jaw configured to open and close relative to the treatment portion, the jaw including:
  - a surface; and
  - a contact surface facing the ultrasound blade, the contact surface configured to be in contact with the treatment portion when the jaw is closed relatively to the treatment portion, wherein the contact surface comprises:
    - a first resin layer positioned on the surface, the first resin layer formed of a first resin, the first resin layer having a first thickness; and
    - a second resin layer layered over the first resin layer, the second resin layer formed of a second resin, the second resin layer having a second thickness, and wherein the second thickness is smaller than the first thickness; wherein:
      - the first resin has a first friction coefficient;
      - the second resin has a second friction coefficient;
      - the first friction coefficient is lower than the second friction coefficient;
      - the first resin has a first abrasion resistance;
      - the second resin has a second abrasion resistance; and
      - the second abrasion resistance is higher than the first abrasion resistance.

14. The ultrasound treatment tool according to claim 13, wherein the contact surface is formed of a coating, and wherein the coating includes the first resin layer and the second resin layer.

15. The ultrasound treatment tool according to claim 14, wherein a plating layer is located between the surface and the contact surface.

16. An ultrasound treatment tool, comprising:
- an ultrasound blade including a treatment portion located at a distal end of the ultrasound blade; and
- a jaw configured to open and close relative to the treatment portion, the jaw including:
  - a surface; and
  - a contact surface facing the ultrasound blade, the contact surface configured to be in contact with the treatment portion when the jaw is closed relative to the treatment portion, wherein the contact surface comprises:
    - a first resin layer formed of a first resin, wherein the first resin is polytetrafluoroethylene (PTFE);
    - a second resin layer layered over the first resin layer, wherein the second resin layer is formed of a mixed resin, wherein the mixed resin is a mixture of the first resin and a second resin, the second resin being polyetheretherketone (PEEK) and wherein:

the first resin layer has a first thickness;

the second resin layer has a second thickness;

the second thickness is smaller than the first thickness;

the first resin has a first friction coefficient;

the second resin has a second friction coefficient;

the first friction coefficient is lower than the second friction coefficient;

the first resin has a first abrasion resistance;

the second resin has a second abrasion resistance; and the second abrasion resistance is higher than the first abrasion resistance.

17. The ultrasound treatment tool according to claim 16 wherein the contact surface comprises a plurality of resin layers, the plurality of resin layers includes the contact surface, the plurality of resin layers is formed of a resin.

* * * * *